United States Patent [19]

Petitte et al.

[11] Patent Number: 5,340,740
[45] Date of Patent: Aug. 23, 1994

[54] METHOD OF PRODUCING AN AVIAN EMBRYONIC STEM CELL CULTURE AND THE AVIAN EMBRYONIC STEM CELL CULTURE PRODUCED BY THE PROCESS

[75] Inventors: James N. Petitte; Zengming Yang, both of Raleigh, N.C.

[73] Assignee: North Carolina State University, Raleigh, N.C.

[21] Appl. No.: 884,423

[22] Filed: May 15, 1992

[51] Int. Cl.$^5$ ............................................. C12N 5/00
[52] U.S. Cl. ........................ 435/240.2; 435/240.21; 435/240.23
[58] Field of Search ........... 435/240.2, 240.21, 240.23, 435/240.3, 240.31; 424/93 U

[56] References Cited

FOREIGN PATENT DOCUMENTS 9003432 4/1990 World Int. Prop. O. .

OTHER PUBLICATIONS

Petitte et al, J. of Cell. Biochem., Supp 13B, (1989) p. 172, Abstract #F114.
J. N. Petite and R. J. Etches *Journal of Cellular Biochemistry The Production of Chimeric Chicks by Embryonic Cell Transfer*. Abstract (1989).
M. Evans et al., *Nature 292,* 154 (1981).
G. Martin, *Proc. Natl. Acad. Sci. USA 78,* 7638 (1981).
A. Smith et al., *Developmental Biology 121,* 1 (1987).
T. Doetschman et al., *Developmental Biology 127,* 224 (1988).
A. Handyside et al., *Roux's Arch Dev. Biol. 198,* 48 (1989).
A. Smith, *J. Tiss. Cult. Meth. 13,* 89 (1991).
J. Nichols et al., *Development 110,* 1341 (1990).
Pease et al., *Developmental Biology 141,* 344 (1990).
M. Evans et al., *PCT Application WO90/03432.*
E. Notarianni et al., *J. Reprod. Fert., Suppl. 41,* 51 (1990).
J. Piedrahita et al., *Theriogenology 34,* 879 (1990).
E. Notarianni et al., *Proceedings of the 4th World Congress on Genetics Applied to Livestock Production,* 58 (Edinburgh, Jul. 1990).
E. Mitrani et al., *Differentiation 21,* 56–61 (1982).
E. Sanders et al., *Cell Tissue Res 220,* 539 (1981).

*Primary Examiner*—Douglas W. Robinson
*Assistant Examiner*—Susan M. Dadio
*Attorney, Agent, or Firm*—Bell, Seltzer, Park & Gibson

[57] ABSTRACT

A method of producing undifferentiated avian cells expressing an embryonic stem cell phenotype is disclosed. The method comprises collecting avian cells from an avian blastoderm prior to formation of the primitive streak, then depositing the avian cells in contact with a mouse fibroblast feeder cell layer, and then growing the avian cells on the mouse fibroblast feeder cell layer in the presence of a media containing leukemia inhibitory factor in a differentiation-inhibiting amount for a time sufficient to produce a sustained avian cell culture. Cell cultures produced by the aforesaid process and veterinary pharmaceutical formulations containing such cells are also disclosed.

10 Claims, 1 Drawing Sheet

METHOD OF PRODUCING AN AVIAN EMBRYONIC STEM CELL CULTURE AND THE AVIAN EMBRYONIC STEM CELL CULTURE PRODUCED BY THE PROCESS

This invention was made with government support under Grant No. 91372056320 awarded by the U.S. Department of Agriculture. The government has certain rights in the invention.

FIELD OF THE INVENTION

The present invention relates to stem cells in general, and particularly relates to avian embryonic stem cells.

BACKGROUND OF THE INVENTION

Embryonic stem cells (ESCs) were first cultured from mouse embryos using a feeder layer of mouse fibroblasts or media conditioned with buffalo rat liver cells. The established ESC lines from mouse embryos have a characteristic phenotype consisting of a large nucleus, a prominent nucleolus, and relatively little cytoplasm. Such cells can be grown relatively indefinitely using the appropriate culture conditions. They can be induced to differentiate in vitro using retinoic acid or spontaneously by removal of the feeder layer or conditioned media. In addition, these cells can be injected into a mouse blastocyst to form a somatic and germ line chimera. This latter property has allowed mouse ESCs to be used for the production of transgenic mice with specific changes to the genome. See M. Evans et al., *Nature* 292, 154 (1981); G. Martin, *Proc. Natl. Acad. Sci. USA* 78, 7638 (1981); A. Smith et al., *Developmental Biology* 121, 1 (1987); T. Doetschman et al., *Developmental Biology* 127, 224 (1988); A. Handyside et al., *Roux's Arch Dev. Biol.* 198, 48 (1989).

The active compound that allows the culture of murine embryonic stem cells has been identified as differentiation inhibiting activity (DIA), also known as leukemia inhibitory factor (LIF). See A. Smith, *J. Tiss. Cult. Meth.* 13, 89 (1991); J. Nichols et al., *Development* 110, 1341 (1990). Recombinant forms of LIF can be used to obtain ESCs from mouse embryos. See S. Pease et al., *Developmental Biology* 141, 344 (1990).

Subsequent to the work with mouse embryos, several groups have attempted to develop stem cell lines from sheep, pig and cow. A few reports indicate that a cell line with a stem cell-like appearance has been cultured from porcine embryos using culture conditions similar to that used for the mouse. See M. Evans et al., PCT Application WO90/03432; E. Notarianni et al., *J. Reprod. Fert., Suppl.* 41, 51 (1990); J. Piedrahita et al., *Theriogenology* 34, 879 (1990); E. Notarianni et al., *Proceedings of the* 4th World Congress on Genetics Applied to Livestock Production, 58 (Edinburgh, July 1990).

Few or no attempts have been made to date regarding the culture of embryonic stem cells from avian embryos. The main reason for this is that it is very difficult to establish a continuous line of chicken cells without viral or chemical transformation, and most primary chicken lines do not survive beyond 2-3 months. The culture of cells from the unincubated embryo has been more difficult, and under reported conditions such cells do not survive beyond two weeks. See E. Mitrani et al., *Differentiation* 21, 56–61 (1982); E. Sanders et al., *Cell Tissue Res.* 220, 539 (1981).

SUMMARY OF THE INVENTION

We have developed a process that allows the culture of cells with an embryonic stem cell phenotype from the avian embryo. The development of this process was problematic. First, we attempted to culture chicken embryo cells on a chicken fibroblast feeder layer. This was not successful. Next, we attempted to culture chicken embryo cells on a mouse feeder layer. This was not successful either. We then attempted to culture chicken embryo cells with BRL conditioned media. This also was not successful. Finally, we cultured chicken embryo cells on a mouse feeder layer in the presence of conditioned media and obtained the cultured stem cells described herein.

A first aspect of the present invention is, accordingly, a method of producing undifferentiated avian cells expressing an embryonic stem cell phenotype. The method comprises collecting avian cells from an avian blastoderm prior to formation of the primitive streak, then depositing the avian cells in contact with a mouse fibroblast feeder cell layer, and then growing the avian cells on the mouse fibroblast feeder cell layer in the presence of a media containing leukemia inhibitory factor in a differentiation-inhibiting amount for a time sufficient to produce a sustained avian cell culture. The sustained avian cell culture consists essentially of undifferentiated avian cells having a large nucleus, a prominent nucleolus, and little cytoplasm (an "embryonic stem cell phenotype"). Typically, the undifferentiated avian cells are capable of maintaining the stem cell phenotype when grown on the mouse fibroblast feeder layer in the presence of the aforesaid media for at least three days, and even for 1, 2, 3, or 4 or more weeks.

A second aspect of the present invention is a sustained avian cell culture consisting essentially of undifferentiated avian cells having a large nucleus, a prominent nucleolus, and little cytoplasm (an "embryonic stem cell phenotype"). The cells are produced from ancestor cells isolated from an avian blastoderm prior to formation of the primitive streak.

A third aspect of the present invention is a veterinary pharmaceutical formulation comprising sustained avian cells as described above with respect to sustained avian cultures in a pharmaceutically acceptable carrier.

While applicants do not wish to be bound to any particular theory of operation of the invention, it appears that the use of an avian feeder cell layer, which would appear the logical choice if one wished to obtain avian embryonic stem cells, actually encourages the cells being cultured to differentiate towards fibroblasts. The solution to this problem appears to be the use of the mouse feeder cell layer. This, however, appears to raise a second problem in that the mouse feeder cell layer alone is insufficient to produce a sustained culture. This second problem appears obviated by the use of a media containing leukemia inhibitory factor in combination with the mouse feeder cell layer.

The foregoing and other objects and aspects of the present invention are explained in greater detail in the figures herein and the specification set forth below.

DETAILED DESCRIPTION OF THE INVENTION

Figure 1:
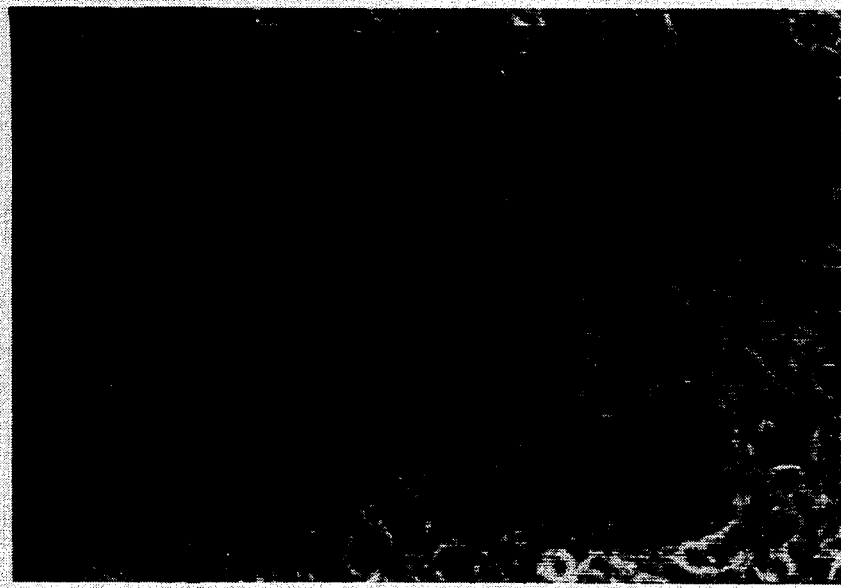
FIG. 1 shows chicken embryonic stem cells (passage 8) cultured on STO feeder cells in BRL-conditioned media 48 hours after passage. Several nests of cells with an embryonic stem cell-like phenotype can be seen.

The term "avian" as used herein refers to any avian species, including but not limited to chicken, turkey, duck, goose, quail and pheasant. Chicken is currently preferred.

The term "sustained" as used herein with respect to cells and cell cultures refers to a cell or cell culture capable of undergoing further cell division, even if the cells are eventually subject to senescence.

The phrase "embryonic stem cell phenotype" refers to undifferentiated avian cells having a large nucleus, a prominent nucleolus, and little cytoplasm.

Avian embryos from which cells are obtained for carrying out the present invention are preferably in a stage prior to formation of the primitive streak, and most preferably in stage IX to XIV of development (i.e., a blastoderm). Such embryos may conveniently be obtained from eggs immediately after they are layed (referred to as "unincubated eggs"). Embryo cells are preferably collected from the central disk of the area pellucida. Other regions could be used, but this dilutes out the desired cells and requires subsequent isolation of desired cell colonies during growth in culture.

The feeder cell layer as used herein is constructed in accordance with procedures known in the art. As noted above, the feeder cell layer preferably consists of mouse fibroblast cells. STO fibroblasts are preferred, but primary fibroblasts are also suitable. Also, while the present invention has been described with respect to the use of mouse cell feeder layers, it is contemplated that feeder layers comprised of cells from other murine species (e.g., rat) or other mammalian species (e.g., ungulate, bovine, and porcine species) may also be used.

The media used in carrying out the present invention may be any suitable media containing leukemia inhibitory factor (LIF) in a differentiation-inhibiting amount. The media may be a conditioned media or a synthetic media containing recombinant LIF, both of which are known in the art. Conditioned media, and particularly BRL conditioned media, is currently preferred.

Cells from the unincubated avian embryo are seeded onto the feeder layer with conditioned media, and the avian cells give rise to nests of cells exhibiting a stem cell phenotype. Unlike the case with mammalian stem cells, it currently appears necessary to have both a suitable feeder layer and conditioned media, since avian ESC-like cells do not appear to survive when transferred to a feeder-layer alone or to BRL-conditioned media alone. The avian embryo cells of the present invention can be cultured for at least one or two months, which is significantly greater than the usual two week life of primary cultures of cells from the unincubated avian embryo.

Cell cultures of the present invention may be formulated for administration to animals by dissociating the cells (e.g., by mechanical dissociation) and intimately admixing the cells with a pharmaceutically acceptable carrier (e.g., phosphate buffered saline solution). Arian cells in such formulations may be prepared to carry a heterologous DNA sequence into an avian subject in the manner described in greater detail below.

Stem cells of the present invention are useful, among other things, as a tool for the study of embryological development (i.e., by labelling the cells with a marker gene and observing their distribution after injection in vivo) and the production of transgenic poultry. They are useful in allowing the application homologous recombination to the production of transgenic poultry.

In avian species, certain donor cell types have been isolated that retain viability when injected into recipient embryos. See Etches et al., in *Avian Incubation*, Chapter 22, Butterworth Publishers (1990); Verrinder Gebbins et al., *Fourth World Congress on Genetics Applied to Livestock Production*, Edinburgh, (1990); Petitte et al., *Development 108*, 185–189 (1990)). These studies showed that blastodermal cells derived from Stage X embryos (embryo at oviposition) remained viable when transferred to comparable recipient Stage X embryos. The present invention provides a new method of altering the phenotype of a bird and the birds so produced with the avian embryonic stem cells disclosed herein. The method comprises transfecting avian embryonic stem cells as disclosed herein with the DNA sequence in vitro (e.g., by electropotation or transformation with a retroviral vector), and then injecting the transfected embryonic stem cells into an egg containing an embryonic bird (e.g., into the yolk sac or onto the chorioallantoic membrane, preferably into the subgerminal cavity, and preferably during early embryonic development (e.g., prior to day 2 or 3 of incubation, and most preferably prior to day 1 of incubation)), with the DNA sequence being effective to cause a change in phenotype in the bird after hatch (e.g., a change in growth rate, feed efficiency, disease resistance, or a combination of all of these factors). Preferably, the egg into which the DNA is introduced is incubated to hatch, and the bird so produced raised to at least an age at which the change in phenotype is expressed. It is of no deleterious consequence if the transformed embryo and bird is chimeric, so long as a physiological response is achieved in the animal after hatch sufficient to evoke the phenotypic change sought.

The mechanism of in ovo injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high speed automated injection system for avian embryos will be particularly suitable for practicing the present invention. Numerous such devices are available, exemplary being the EMBREX INOVOJECT TM system (described in U.S. Pat. Nos. 4,681,063 and 4,903,625 to Hebrank), and U.S. Pat. Nos. 4,040,388, 4,469,047, and 4,593,646 to Miller. The disclosure of these references and all references cited herein are to be incorporated herein by reference. All such devices, as adapted for practicing the present invention, comprise an injector containing the embryonic stem cell as described herein, with the injector positioned to inject an egg carried by the apparatus with the DNA. In addition, a sealing apparatus operatively associated with the injection apparatus may be provided for sealing the hole in the egg after injection thereof.

The DNA sequence introduced in ovo with embryonic stem cells of the invention is, in general, a construct comprised of a promoter functional in avian cells and a gene encoding a peptide or protein operably linked to the promoter. Preferably, the protein or peptide is physiologically active and capable of producing a phenotypic change in the bird. In general, the DNA construct may be a linear DNA sequence (introduced into the embryonic stem cells of the invention by electroporation) or a sequence carried by a vector or other suitable carrier for transforming the embryonic stem cells of the invention, such as liposomes, calcium phosphate, or DMSO. Vectors, as discussed below, may be plasmids, viruses (including retroviruses), and phage, whether in native form or derivatives thereof.

Illustrative of genes encoding a protein or peptide are those which encode a protein or peptide selected from the group consisting of growth hormone, thyroid releasing hormone (TRH), Marek's MDX, and immunogenic recombinant antigens such as that for coccidiosis.

The production of cloned genes, recombinant DNA, vectors, transformed host cells, proteins and protein fragments by genetic engineering is well known. See e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26to Col. 14 line 12. Protocols for restriction endonuclease digestion, preparation of vectors, DNA purification and other such procedures were essentially as described in standard cloning manuals. See Sambrook et al., *Molecular Cloning, a Laboratory Manual*, (2d Ed., Cold Spring Harbor Press, N.Y. (1989)).

A vector is a replicable DNA construct used herein to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription, enhancer elements which can stimulate transcription many-fold from linked heterologous promoters, a splice acceptor and/or donor sequences, and termination and polyadenylation signals. Also required is the sequence for a ribosome binding site capable of permitting translation which is operably linked to the gene to be expressed. Recently, a muscle-specific promoter has been isolated which is positioned upstream of both the skeletal muscle structural gene and the essential proximal promoter element and is operably associated with each. (Mar and Ordahl, *Proc. Natl. Acad. Sci. USA 85*, 6404–6408 (1988)). Vectors comprise plasmids, viruses (e.g. adenovirus, cytomegalovirus), phage, and DNA fragments integratable into the host genome by recombination. The vector replicates and functions independently of the host genome, or may in some instances integrate into the genome itself.

The present invention is explained in greater detail in the following non-limiting Examples.

EXAMPLE 1

Preparation of Feeder Cells

Gelatinizing culture dishes are prepared as follows. First, 0.1% gelatin is added to water to prepare a gelatin solution, which is then autoclaved. 4 ml of the gelatin solution is added to each plate for 6 cm plates, or 2 ml/well of gelatin solution is added to each well for 12-well plates. The plates or wells are incubated at 4° C. for 30 minutes, and the gelatin aspirated prior to use.

STO feeder cells (American Type Culture Collection No. CRL 1503) are prepared by culturing STO cells to 80% confluency in DMEM with 10% FBS. The cells are then treated with mitomycin C at 10 $\mu$g/ml for 2–3 hours, after which they are rinsed three times with PBS. After rinse, the cells are trypsinized with a 0.25% trypsin/0.025% EDTA solution, the cells collected in DMEM with 10% FBS, and washed at 1,000 rpm for 5 min. After washing, cells are suspended in 5 ml of DMEM w. 10% FBS and counted. The cells are then seeded onto gelatinized plates prepared as described above at a density of $1 \times 10^5$/cm$^2$ and incubated overnight before use.

Primary Chicken Embryonic fibroblasts are prepared by harvesting fibroblasts from 10-day old chick embryos, subculturing the cells once, and then preparing the cells as feeder cells as listed for STO cells above.

EXAMPLE 2

Preparation of Conditioned Media

Buffalo Rat Liver (BRL) cell conditioned media is prepared by culturing BRL-3A cells (American Type Culture Collection No. CRL 1442) in DMEM w/10% FBS to confluency, then adding 13 ml of DMEM/10%FBS to each 75cm$^2$ flask. Media is collected from the flask every third day, with each flask being collected three to four times. Media is stored at $-20°$ C. For use, the media is filtered, adjusted to pH 7.5 with HCl, diluted to 80% BRL-CM with DMEM supplemented with 15% FBS, and the diluted conditioned media then supplemented with 0.1 mM $\beta$-mercaptoethanol.

LMH (chicken liver cell) conditioned media is prepared by culturing LMH cells in the same manner as for BRL-3A cells above, and the conditioned media prepared in the same manner as BRL-conditioned media as given above.

EXAMPLE 3

Isolation of Unincubated Chick Embryo Cells

To isolate stages IX–XIV embryo cells, the surface of a fertilized chicken egg is sterilized with 70% ethanol, the egg opened, and the yolk separated from the albumen. The yolk is then placed in a petri dish with the blastoderm in the uppermost position. A filter paper ring is placed over the blastoderm and the yolk membrane cut around the periphery of the ring. The filter paper ring with the embryo is then transferred to PBS with the ventral side uppermost, excess yolk removed, the embryo teased from the yolk membrane, the embryo transferred to cold PBS and rinsed with PBS. PBS is then removed, trypsin added, and the embryo incubated for 10 min. at 4° C. DMEM/10% FBS is added, the cells pelleted by centrifugation, the supernatant removed, and the cells resuspended in 80% BRL-CM. Embryo cells are then seeded onto the appropriate culture system.

EXAMPLE 4

Culturing of Arian Embryonic Stem Cells

Using the procedures given above several methods of culturing cell with an embryonic stem cell phenotype from unincubated chicken embryos were carried out.

First, 10 whole embryos at stage X were isolated, dissociated, seeded onto chicken embryonic fibroblast feeder layers, and cultured with 80% BRL-CM. A significant amount of differentiation occurred, mainly cells of a fibroblast-like phenotype. Only a few clusters of cells remained relatively undifferentiated and contained large amounts of lipid. These cells grew slowly, if at all, and were lost by the second passage.

Figure 2:
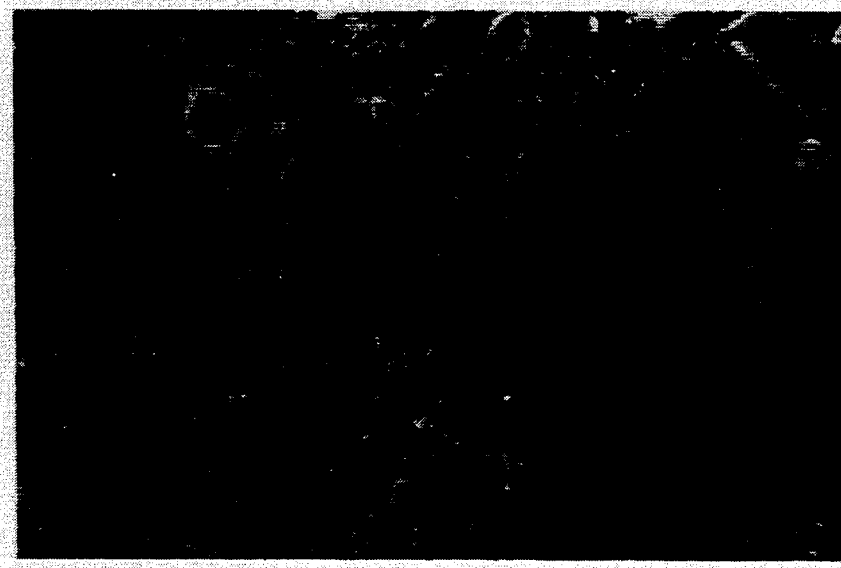
FIG. 2 shows a confluent layer of chicken embryonic stem cells ready for passage. Stem cell colonies have expanded to join each other.

Second, 10 whole embryos at stage X were isolated, dissociated, seeded onto STO feeder layers, and cultured with 80% BRL-CM. Upon culture, the cells attached to the feeder layer and grew as small flattened colonies. In the first 3 passages, the cells lost all lipid droplets and exhibited a phenotype and growth characteristics similar to that observed for murine and porcine embryonic stem cells. Specifically, the cells contained a large nucleus with a prominent nucleolus and relatively little cytoplasm (see FIG. 1 and FIG. 2). The cells grew in nests with a generally uniform phenotype. Each nest remained a single cell thick as it grew, a characteristic shared with porcine, but not murine, embryonic stem cells. Unlike either murine or porcine cells, the nests of chicken embryonic stem cells exhibited the tendency to invade the feeder layer, pushing the STO feeder cells to the side or growing underneath the feeder layer. It was possible to culture these cells for 23 passages. In general, $10^6$ cells were seeded onto a STO feeder layer in a 6 cm dish and in 2-3 days $2 \times 10^6$ to $5 \times 10^7$ CES cells could be obtained.

On the fifth passage, a portion of the CES cells were transferred to BRL-CMmedia alone. Initially, the CES cells grew rapidly and formed large ES-like colonies. When passed onto new gelatinized plates in BRL-CM, the cells differentiated into fibroblast-like cells, accumulated lipid droplets and died with the nest passage. Likewise, at the tenth passage a portion of the CES cells grown on STO cells and in BRL-CM were seeded onto STO feeder cells alone. These cells also became fibroblast-like, and could not be maintained on STO feeder cells alone. These observation suggest that the culture of chicken embryonic stem cells requires both a feeder layer and conditioned media.

EXAMPLE 5

Initiating and Maintenance of Chicken Embryonic Stem (CES) Cells

Chicken embryonic stem cells are initiated by isolating stage IX-XIV unincubated chicken embryos, and the area pellucida used as the source of cells for culture. Cells are seeded onto mitotically inactivated STO feeder layers with 80% BRL-CM and DMEM supplemented with 15% FBS and 0.1 mM β-mercaptoethanol. After the initial seeding, the phenotype of the chicken cells is observed daily. Eventually, a portion of the cells begin to lose their lipid droplets and begin to invade the feeder layer while remaining a closely packed nest of cells generally one cell thick. During the first few passages, the entire culture is passed onto new STO feeder layers until several nests of stem cell-like cells appear. Once an initial culture shows several nests of stem cells, the cultures are maintained by trypsinizing the culture and counting the number of chicken embryonic stem cells. About 0.3 to $1 \times 10^6$ CES cells are seeded onto new STO feeder layers. The cultures are fed twice each day with BRL-CM and passed onto new feeder layers every 2-3 days, depending upon the density of the CES cells. Using this procedure, CES cells have been maintained for 23 passages (approximately two months). Data are given in Table 1 below.

TABLE 1

Yield of CES cells with each passage. Chick embryo cells were seeded at $3.5 \times 10^5$ cells/6 cm plate at day 0. $1 \times 10^6$ cells were seeded with each passage.

| Day of Culture | Passage Number | Total CES $\times 10^6$ |
|---|---|---|
| 23 | 9 | 3.0 |
| 25 | 10 | 3.5 |
| 27 | 11 | 4.0 |
| 29 | 12 | 2.0 |
| 31 | 13 | 1.5 |
| 34 | 14 | 3.0 |
| 37 | 15 | 1.3 |
| 38 | 16 | 2.0 |
| 42 | 17 | 2.5 |
| 44 | 18 | 3.0 |
| 49 | 19 | 1.0 |
| 51 | 20 | 1.6 |
| 53 | 21 | .7 |

The foregoing examples are illustrative of the present invention, and are not to be construed as limiting thereof. The invention is defined by the following claims, with equivalents of the claims to be included therein.

That which is claimed is:

1. A method of producing a sustained culture of undifferentiated avian cells expressing an embryonic stem cell phenotype, comprising:

collecting avian cells from an avian blastoderm prior to formation of the primitive streak;

depositing said avian cells in contact with a mouse fibroblast feeder cell layer;

growing said avian cells on said mouse fibroblast feeder cell layer in the presence of a media containing leukemia inhibitory factor in a differentiation-inhibiting amount for a time sufficient to produce a sustained avian cell culture;

said sustained avian cell culture consisting essentially of undifferentiated avian cells expressing an embryonic stem cell phenotype.

2. A method according to claim 1, wherein said avian cells are collected from the area pellucida of a stage IX to stage XIV blastoderm.

3. A method according to claim 1, wherein said undifferentiated avian cells are capable of maintaining said stem cell phenotype when grown on said mouse fibroblast feeder layer in the presence of said media for at least three days.

4. A method according to claim 1, wherein said avian blastoderm is a blastoderm selected from the group consisting of chicken, turkey, duck, geese, quail and pheasant blastoderms.

5. A method according to claim 1, wherein said avian blastoderm is a chicken blastoderm.

6. A method according to claim 1, wherein said media is a conditioned media.

7. A method according to claim 1, wherein said mouse fibroblast feeder cell layer is a mouse STO fibroblast feeder cell layer.

8. A sustained avian cell culture of undifferentiated avian cells expressing an embryonic stem cell phenotype produced by the process of claim 1.

9. A method of producing a sustained culture of undifferentiated chicken cells expressing an embryonic stem cell phenotype, comprising:

collecting avian cells from the area pellucida of a stage IX to stage XIV chicken blastoderm;

depositing said avian cells on contact with a mouse STO fibroblast feed cell layer;

growing said avian cells on said mouse fibroblast feeder cell layer in the presence of a conditioned media containing leukemia inhibitory factor in a differentiation-inhibiting amount of a time sufficient to produce a sustained avian cell culture;

said sustained avian cell culture consisting essentially of undifferentiated avian cells expressing an embryonic stem cell phenotype, and wherein said undifferentiated avian cells are capable of maintaining said stem cell phenotype when grown on said mouse fibroblast feeder layer in the presence of said media for at least three days.

10. A sustained chicken cell culture of undifferentiated chicken cells expressing an embryonic stem cell phenotype produced by the process of claim 9.

* * * * *

UNITED STATES PATENT AND TRADEMARK OFFICE
CERTIFICATE OF CORRECTION

PATENT NO. : 5,340,740
DATED : August 23, 1994
INVENTOR(S) : James N. Petitte and Zengming Yang It is certified that error appears in the above-indentified patent and that said Letters Patent is hereby corrected as shown below:

Column 3, line 63, please correct " Arian " to read
-- Avian --.

Column 4, line 21, please correct " electropotation "
to read -- electroporation --.

Column 4, line 22, please correct " retrovital " to read
-- retroviral --.

Column 7, line 2, please correct " Arian " to read
-- Avian --.

Signed and Sealed this

Sixth Day of December, 1994

Attest:

BRUCE LEHMAN

*Attesting Officer*     *Commissioner of Patents and Trademarks*